United States Patent
Bumgarner et al.

(10) Patent No.: US 7,832,675 B2
(45) Date of Patent: Nov. 16, 2010

(54) METHOD AND APPARATUS FOR TENSILE TESTING AND RETHREADING OPTICAL FIBER DURING FIBER DRAW

(75) Inventors: Kirk P. Bumgarner, Wilmington, NC (US); Kenneth W. Roberts, Wilmington, NC (US); David A. Tucker, Wilmington, NC (US)

(73) Assignee: Corning Incorporated, Corning, NY (US)

( * ) Notice: Subject to any disclaimer, the term of this patent is extended or adjusted under 35 U.S.C. 154(b) by 1116 days.

(21) Appl. No.: 10/800,551

(22) Filed: Mar. 15, 2004

(65) Prior Publication Data

US 2004/0172978 A1 Sep. 9, 2004

Related U.S. Application Data

(62) Division of application No. 09/733,352, filed on Dec. 8, 2000, now abandoned.

(60) Provisional application No. 60/173,401, filed on Dec. 28, 1999.

(51) Int. Cl.
*B65H 65/00* (2006.01)
*B65H 57/00* (2006.01)

(52) U.S. Cl. .............. 242/474.7; 242/476.1; 242/476.6; 242/157.1

(58) Field of Classification Search ............... 242/474.4, 242/474.5, 474.6, 474.7, 483.3, 483.5, 473.7, 242/473.8, 476.6, 476.1, 157.1; 226/92, 226/11; 65/479, 539

See application file for complete search history.

(56) References Cited

U.S. PATENT DOCUMENTS 4,148,218 A * 4/1979 Knowles et al. ............... 73/829

(Continued)

FOREIGN PATENT DOCUMENTS

EP 0 873 962 10/1998

(Continued)

OTHER PUBLICATIONS

Patent Abstracts of Japan—Publication No. 62091441, Sumitomo Electric Ind Ltd, Apr. 25, 1987.

(Continued)

*Primary Examiner*—Evan H Langdon
(74) *Attorney, Agent, or Firm*—Robert L. Carlson (57) ABSTRACT

A method and apparatus for automatic threading and winding of optical fiber onto various components in a fiber draw system, as well as methods and apparatus for conducting online tensile screening of optical fiber at high speeds. In a preferred embodiment, the fiber is tensile tested during fiber draw and wound directly onto a shipping spool to be shipped to a customer. The tensile stress can be imparted to the fiber during the draw process by feeding the fiber through a screener capstan, which works in conjunction with another capstan to impart the desired tensile stress to the fiber during the draw process. Another aspect is a method and apparatus for threading or rethreading of a moving length of fiber through a fiber draw or fiber testing process, in which fiber is wound onto a spool, comprising activating an aspirator to obtain the fiber at a first location and moving said aspirator in at least two dimensions to thereby move the fiber to a second location and thread the fiber through or onto at least one component in the fiber draw or testing process.

12 Claims, 6 Drawing Sheets

U.S. PATENT DOCUMENTS

| | | | | |
|---|---|---|---|---|
| 4,184,555 | A | * | 1/1980 | Maltby et al. ............... 177/208 |
| 4,206,883 | A | * | 6/1980 | Isoard .................... 242/476.1 |
| 4,291,841 | A | | 9/1981 | Dalrymple et al. ............ 242/18 |
| 4,331,463 | A | | 5/1982 | Briere et al. .................... 65/13 |
| 4,601,208 | A | * | 7/1986 | McKay et al. ................. 73/829 |
| 4,696,438 | A | | 9/1987 | Myers .................... 242/118.41 |
| 4,891,933 | A | * | 1/1990 | Raasch ......................... 57/269 |
| 4,892,572 | A | | 1/1990 | Tsuneishi et al. ............. 65/10.1 |
| 4,938,432 | A | * | 7/1990 | Kurt et al. ................... 242/580 |
| 4,958,926 | A | * | 9/1990 | Bu-Abbud ................ 356/73.1 |
| 5,000,541 | A | * | 3/1991 | DiMarcello et al. ......... 385/128 |
| 5,076,104 | A | * | 12/1991 | Glaesemann et al. .......... 73/830 |
| 5,322,228 | A | | 6/1994 | Nagayama et al. ........ 242/18 R |
| 5,410,396 | A | | 4/1995 | Rochester ................. 356/73.1 |
| 5,787,216 | A | * | 7/1998 | Bice et al. ..................... 385/97 |
| 5,922,098 | A | * | 7/1999 | Tsuneishi et al. ............. 65/384 |
| 6,027,062 | A | | 2/2000 | Bacon et al. ............. 242/474.7 |
| 6,318,166 | B1 | * | 11/2001 | Roos ........................... 73/160 |

FOREIGN PATENT DOCUMENTS

| | | | |
|---|---|---|---|
| JP | 62-91441 | | 4/1987 |
| JP | 3-153539 | | 7/1991 |
| JP | 4-164227 | * | 6/1992 |
| JP | 4-213040 | * | 8/1992 |
| JP | 11-83672 | * | 3/1999 |
| WO | WO 00/39013 | | 7/2000 |
| WO | WO 00/40495 | | 7/2000 |

OTHER PUBLICATIONS

Patent Abstracts of Japan—Publication No. 60179626, Nippon Telegr & Teleph Corp, Sep. 13, 1985.

Patent Abstracts of Japan—Publication No. 01069536, Furukawa Electric Co Ltd, Mar. 15, 1989.

Patent Abstracts of Japan—Publication No. 01069537, Furukawa Electric Co Ltd, Mar. 15, 1989.

Patent Abstracts of Japan—Publication No. 03153539, Sumitomo Electric Ind Ltd, Jul. 1, 1991.

Patent Abstracts of Japan—Publication No. 58208639, Hitachi Cable Ltd, Dec. 5, 1983.

* cited by examiner

METHOD AND APPARATUS FOR TENSILE TESTING AND RETHREADING OPTICAL FIBER DURING FIBER DRAW

CROSS-REFERENCE TO RELATED APPLICATIONS

This is application is a divisional of U.S. application Ser. No. 09/733,352,filed Dec. 8, 2000 now abandoned, which claims the benefit of U.S. Provisional Patent Application Ser. No. 60/173,401 filed on Dec. 28, 1999, the content of which is relied upon and incorporated herein by reference in its entirety, and the benefit of priority under 35 U.S.C. §120 is hereby claimed.

FIELD OF THE INVENTION

The present invention relates to a method and apparatus for automatic threading and winding of optical fiber onto various components in a fiber draw system. The invention further relates to methods and apparatus for conducting online tensile screening of optical fiber at high speeds and winding of the screened optical fiber directly onto optical fiber shipping spools.

BACKGROUND OF INTRODUCTION

Optical waveguide fibers (optical fibers) are a well-known transmission medium used in optical communication systems. Fiber draw manufacturing techniques are known wherein the optical fiber is drawn from an optical fiber preform and wound onto a spool. In the past, the drawing of optical fiber has typically involved winding of the fiber onto bulk spools that may hold up to 400 km of fiber. The bulk spool is then typically manually transported to an off-line rewinding machine that is threaded manually by an operator. The off-line machine rewinds fiber from the bulk spool to a plurality of smaller shipping spools. Prior to or during the transfer of the fiber from the bulk spool to the smaller shipping spools, various tests are conducted on the fiber. For example, the same machine used to wind the fiber from the bulk spool to the shipping spool is also commonly employed to apply a predetermined minimum level of stress (typically 100 kpsi) to the fiber to make sure the fiber meets the minimum strength requirements. This application of stress is commonly called screening or proof testing. The machine stops winding to the shipping spool when screening breaks occur, and the operator must then manually rethread the machine again and begin winding the fiber onto a new spool.

It would be desirable to conduct tensile strength proof testing on the fiber during the fiber draw process, before it is wound onto a storage spool, which preferably is a shipping spool. However, with the high draw speeds (e.g. greater than 20-25 m/s) employed in some of today's fiber manufacturing operations, such online proof testing has not been achievable. For one thing, online screening would increase the number of fiber breaks in the fiber at the draw, due to the added tensile stress applied to the fiber to proof test it. In addition, because the fiber draw process cannot be stopped, there would be a great deal of lost fiber while the operator rethreaded the online tensile screening equipment. Of course at the higher draw speeds (e.g. greater than 20 m/s) employed in many of today's fiber draw processes, the fiber being threaded would somehow also have to keep up with the length of fiber being fed by the fiber draw process. Also, because of the time involved with threading conventional tensile testing apparatus, using conventional techniques a great deal of fiber would be lost during the rethreading operation. As a result, manufacturers have thus far instead had to resort to manufacturing processes wherein they draw the fiber at lower draw tensions onto relatively large (e.g. can store 400 km or more) bulk spools. These fiber on these bulk spools is then proof tested off-line, during or prior to its being wound onto smaller shipping spools.

SUMMARY OF THE INVENTION

One aspect of the present invention relates to a method of tensile proof testing an optical fiber during a fiber draw process, comprising pulling a length of optical fiber from an optical fiber preform at a fiber draw speed greater than 20 m/s, imparting a desired tensile stress to said fiber to thereby test the strength of said fiber and subsequent to said imparting a tensile stress, winding said fiber onto a spool. The tensile stress applied to the fiber preferably is equal to a desired proof testing force. Preferably the desired tensile stress is greater than about 80 psi, and more preferably the desired tensile stress is greater than about 95 psi.

In a preferred embodiment, the fiber is wound directly onto a shipping spool to be shipped to a customer. Preferably the shipping spool is not capable of holding more than 150 km, more preferably not more than 100 km, and most preferably not more than about 75 km of optical fiber. Such shipping spools can then be shipped directly to a customer without having to be rewound onto smaller spools. Preferably, the shipping spool is one which enables access to both ends of said fiber on said spool, and the fiber is wound onto said shipping spool in a manner which enables both ends of said fiber to be accessed while said fiber is stored on said spool. In this way, optical properties testing and other forms of testing can be conducted on the fiber while stored on the spool, without having to remove the fiber from the spool. For example, the fiber can be tested by a testing method which involves connecting one end of said fiber on the spool to a light source, launching light from the light source through the fiber, and evaluating the properties of the light at the other end of the fiber. Examples of such tests include optical time domain reflectometry (OTDR), which is used to measure the amount of dispersion per unit length in the fiber, as well as dispersion geometry and polarization mode dispersion.

The tensile stress can be imparted to the fiber during the draw process by feeding the fiber through a screener capstan, which works in conjunction with another capstan to impart the desired tensile stress to the fiber during the draw process. For example, the screener capstan may be located downstream of another capstan and rotated at a higher circumferential speed than the other capstan to thereby pull the fiber and impart a desired tensile stress. Preferably, the fiber tension between the two capstans is monitored during the draw process and the speed of the screener capstan adjusted in response to the monitored tension, to thereby constantly maintain a desired tensile screening force or range of forces. For example, the tension in the fiber can be monitored via a load cell (for example, which may be located between the two capstans) operatively connected to a pulley, which in turn contacts the fiber. A computer can be used to monitor the tension in said fiber via the load cell and adjust the speed of the screener capstan accordingly. Alternatively, other methods could be employed to impart the desired amount of tensile stress to the fiber during the draw process. For example, such stress could be applied using a weight which is applied onto a pulley around which the fiber travels during the draw process. Alternatively, the fiber could be wound around two capstans which are mechanically linked so that one of the capstan travels at a higher circumferential speed than the other capstan. A still further alternative would be to have the fiber travel around a pulley having two different adjacent fiber track channels, each fiber track channel having different circumferences, the difference in circumferences being selected to provide a desired tensile force onto the fiber as it passes through the two track channels of the pulley.

Another aspect of the invention relates to a method and apparatus for threading or rethreading of a moving length of fiber through a fiber draw or fiber testing process, in which fiber is wound onto a spool, comprising activating an aspirator to obtain the fiber at a first location and moving said aspirator in at least two dimensions to thereby move the fiber to a second location and thread the fiber through or onto at least one component in the fiber draw or testing process. The moving length of fiber can be, for example, a moving length of fiber in a fiber draw process or an off-line fiber screening process. In a preferred embodiment, the aspirator is moved to guide the fiber onto at least one guide pulley, after which the fiber is moved proximate to the winding spool, where it is engaged and the fiber is wound upon the spool. For example, the fiber length may be engaged by a snagger tooth or other device capable of grabbing the fiber on the storage spool. Immediately after the fiber is engaged by the rotating spool, the fiber is cut to separate the fiber from the aspirator. The guide pulley in this case and the fiber storage spool then traverses with respect to one another to wind the fiber onto the spool.

In another embodiment, the method further comprises orienting at least a first, second, and third pulley so that, when the aspirator moves said fiber to said second location, the pulleys are disposed along the length of said fiber and on alternating sides of said desired fiber. The second pulley is then moved across the path of the fiber to thereby retain the fiber in contact with the first, second, and third pulleys, thereby causing the fiber to move in a serpentine path.

In still another embodiment, the aspirator is used together with another, separate fiber guiding device, to guide the fiber through at least one component in a fiber winding system. For example, a mechanical guide finger assembly can be used to engage a portion of the fiber, between the source of the fiber and the aspirator. The guide finger can then bend and move the path of the moving optical fiber and thereby guide the fiber onto or through the component to be threaded. Preferably, the guide finger is a cylindrical member over which the fiber may travel freely and continue to be collected by the aspirator. Such a guide member could be in the form of a hook or J-shaped member, or more preferably is a cylindrical tube or rod, which may or may not be rotatable around its axis to facilitate free travel of the fiber over the guide finger.

Another aspect of the invention relates to an apparatus for drawing and winding fiber onto a spool, and prooftesting the fiber after drawing of the fiber but prior to the fiber being wound onto the spool. The apparatus includes a furnace for softening an optical fiber preform sufficiently that a fiber can be drawn therefrom; a first capstan of other fiber drawing device designed to draw fiber from the preform at a rate exceeding 20 m/s, and preferably exceeding 25 m/s, and a prooftesting device. The prooftesting device preferably includes the first capstan device (also known as the tractor capstan assembly) located downstream of the furnace including at least one wheel and a motor for driving the wheel at a first circumferential speed, and a second capstan assembly including at least one wheel and a servo motor for driving the wheel at a second circumferential speed so that the difference between the first and second circumferential speeds creates a desired proof testing tensile stress which is applied to the fiber. A load cell is preferably operatively connected to the fiber (e.g., between the two capstans) for monitoring tension in the fiber. A computer control is provided for receiving input from the load cell and adjusting the speed of the first or second capstan assemblies to aid in maintaining a uniform tensile stress or within a desired range of tensile stress.

The automatic rewinding methods and apparatus described herein enable a number of advantages over the prior art. For one thing, by using the aspirator and guide finger in the manner and method disclosed herein to rethread the optical fiber through various components of the fiber winding system, fiber can continuously be removed and discarded from the manufacturing process as it is simultaneously being threaded through the system. Consequently, the supply of fiber does not have to be stopped in order to rewind or rethread the system. Using the techniques disclosed herein, an entire on-line winding system, including an on-line prooftesting section, can be rewound in less than 10 seconds. In fact, using the methods and apparatus disclosed herein, rewinding of the entire fiber winding system, including an on-line fiber tensile strength screening device, has been achieved on line during a experimental fiber draw operation in less than 7 seconds. This includes providing a fresh shipping spool, guiding the fiber into winding engagement with the new spool, and beginning winding of the fiber to the new spool. Because the present invention enables rethreading of the fiber winding system in such a short period of time, on-line proof testing can be achieved, even at draw speed of 25-30 m/sec. or more, without having to worry about losing a significant amount of fiber.

On-line screening of the fiber in turn enables the fiber to be wound directly onto shipping spools, rather than large bulk storage spools, thus greatly reducing or even totally eliminating the costs associated with the previous method of drawing the fiber onto a bulk spool, conducting off-line proof-testing, and then winding the fiber onto shipping spools.

By winding the fiber onto a spool capable of providing access to both ends of the fiber, and by selecting the length of fiber wound on the spool to be short enough (e.g. less than 150 km, more preferably less than 100 km, and most preferably less than 75 km), any optical measurements that are to be conducted on the fiber can be done while the fiber is stored on the spool. Consequently, the fiber can be drawn from an optical fiber preform at high speed (e.g., greater than 20, more preferably greater than 25, and most preferably greater than 30 m/s), tensile tested during the fiber draw process, and then wound onto a fiber storage spool. The fiber could then be tested off-line while stored on the fiber storage spool for any additional (e.g. other optical) desired measurements, and then shipped directly to a customer (e.g. a fiber optic cable company who then cables various strands of optical fiber into an optical fiber cable) without ever having to rewind the fiber onto a different spool.

Also, because the automatic rewinding methods and apparatus disclosed herein greatly facilitate and speed up the fiber rewinding process, fiber can now be selectively removed during the fiber draw operation if desired without the loss of significant amounts of fiber. For example, if fiber is detected that has a diameter (e.g. fiber or coating diameter) that is out of specification, the defective fiber can be cut, and the bad fiber allowed to be collected and discarded into the aspirator, until good (i.e., in specification) fiber is again detected, after which time the fiber is wound onto the ondraw sceener and onto a fiber storage spool.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DETAILED DESCRIPTION OF THE INVENTION

Figure 1:
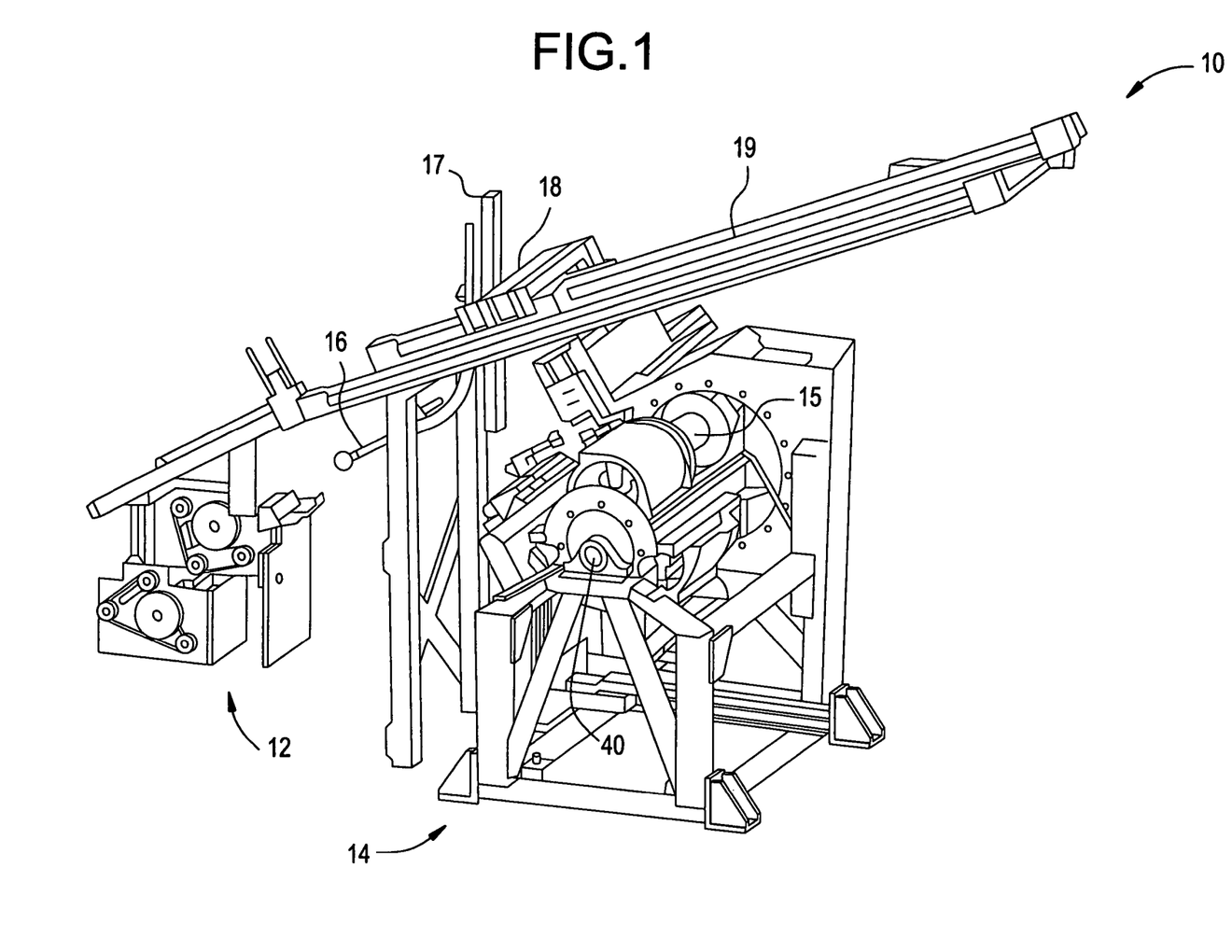
FIG. 1 is a perspective view of a preferred embodiment of a winding apparatus according to the present invention.
Figure 2:
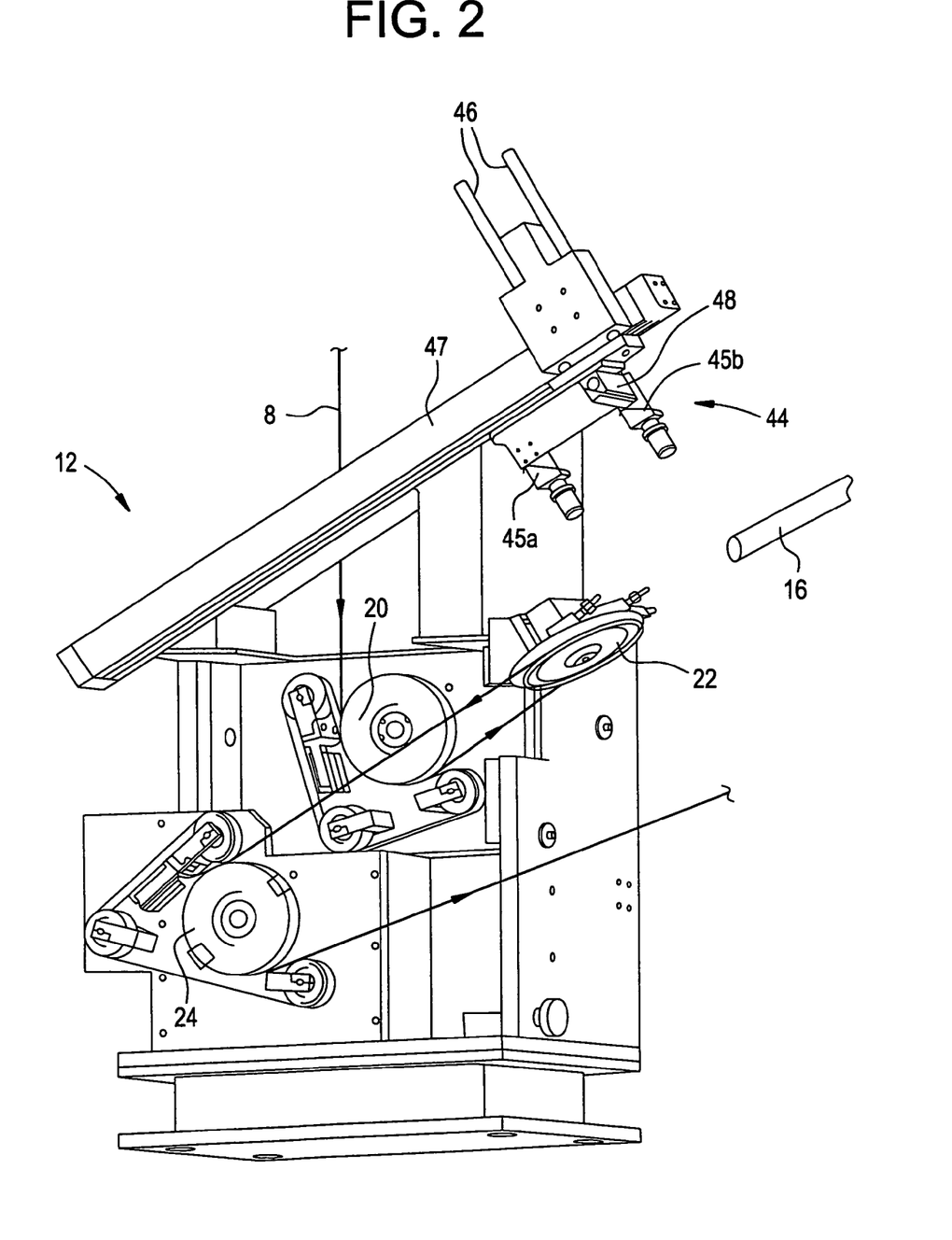
FIG. 2 is an enlarged perspective view of the screener section of the winding apparatus of FIG. 1.
Figure 3:
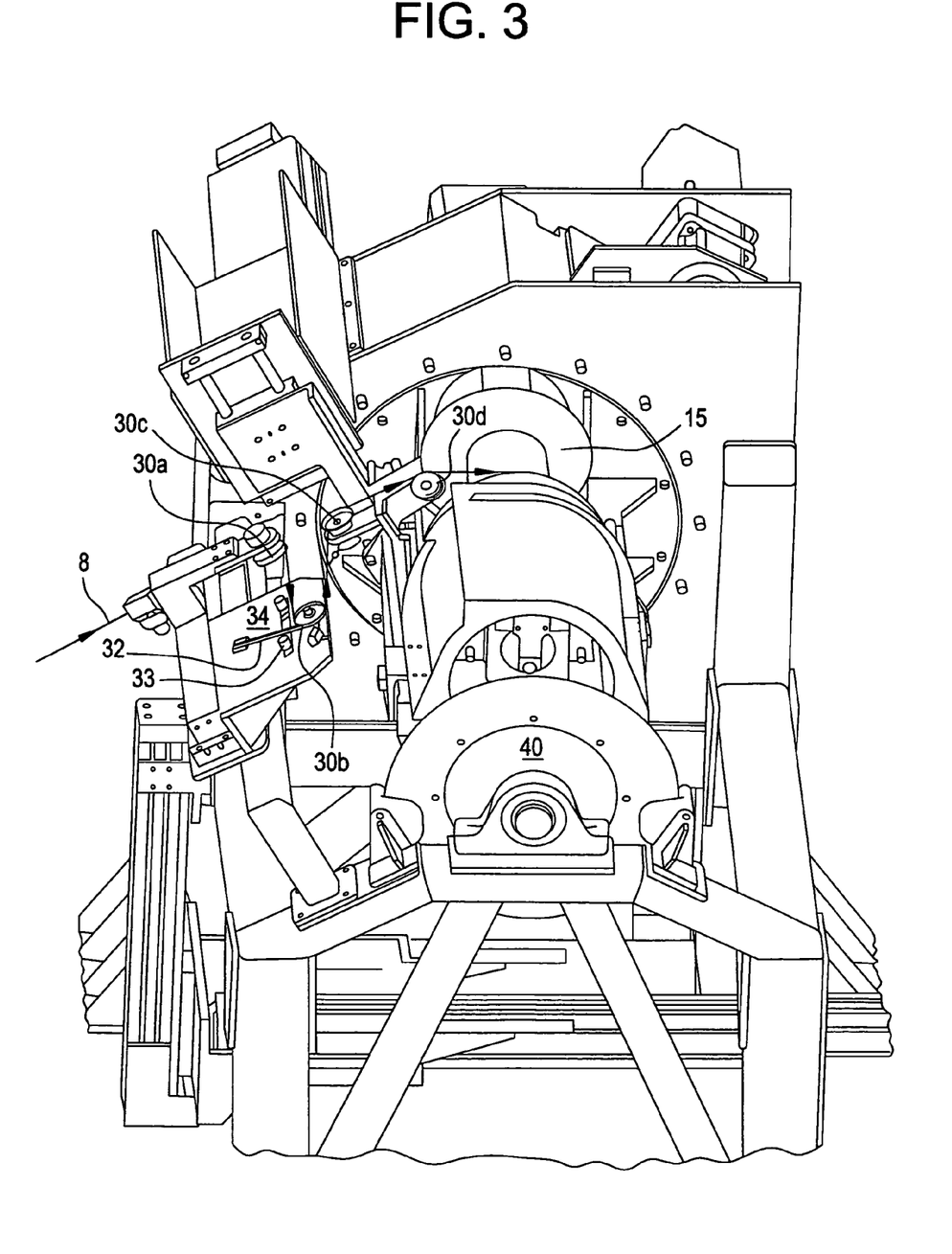
FIG. 3 is an enlarged perspective view of the spool winding section of the winding apparatus of FIG. 1.

FIGS. 1, 2, and 3 illustrate a preferred optical fiber winding system 10 in accordance with the present invention, wherein optical fiber 8 is drawn directly from an optical fiber preform or draw blank in an optical fiber draw process. As illustrated in FIG. 1, the major components of the system include a screening section 12, where the fiber is proof tested, and a winding section 14, where the fiber is wound onto a fiber storage spool 15.

The fiber is mechanically stressed a desired amount (i.e., proof tested) while traveling through screener section 12 which is illustrated in FIGS. 1 and 2. The fiber is then wrapped directly onto spool 15 in fiber winder section 14, illustrated in FIGS. 1 and 3. Spool 15 preferably is a shipping spool which is either to be shipped directly to a customer, which may be a purchaser of optical fiber and/or a cable manufacturing plant to be cabled directly without having to be respooled onto another fiber storage spool. In this way, from the time the fiber is first drawn into an optical fiber until the fiber is cabled into an optical fiber cable, the fiber may be stored on a single storage spool, without having to endure transfer to successive storage spools, between the time at which the fiber is manufactured and the time the fiber is shipped to a customer, to enable various testing procedures.

Figure 6:
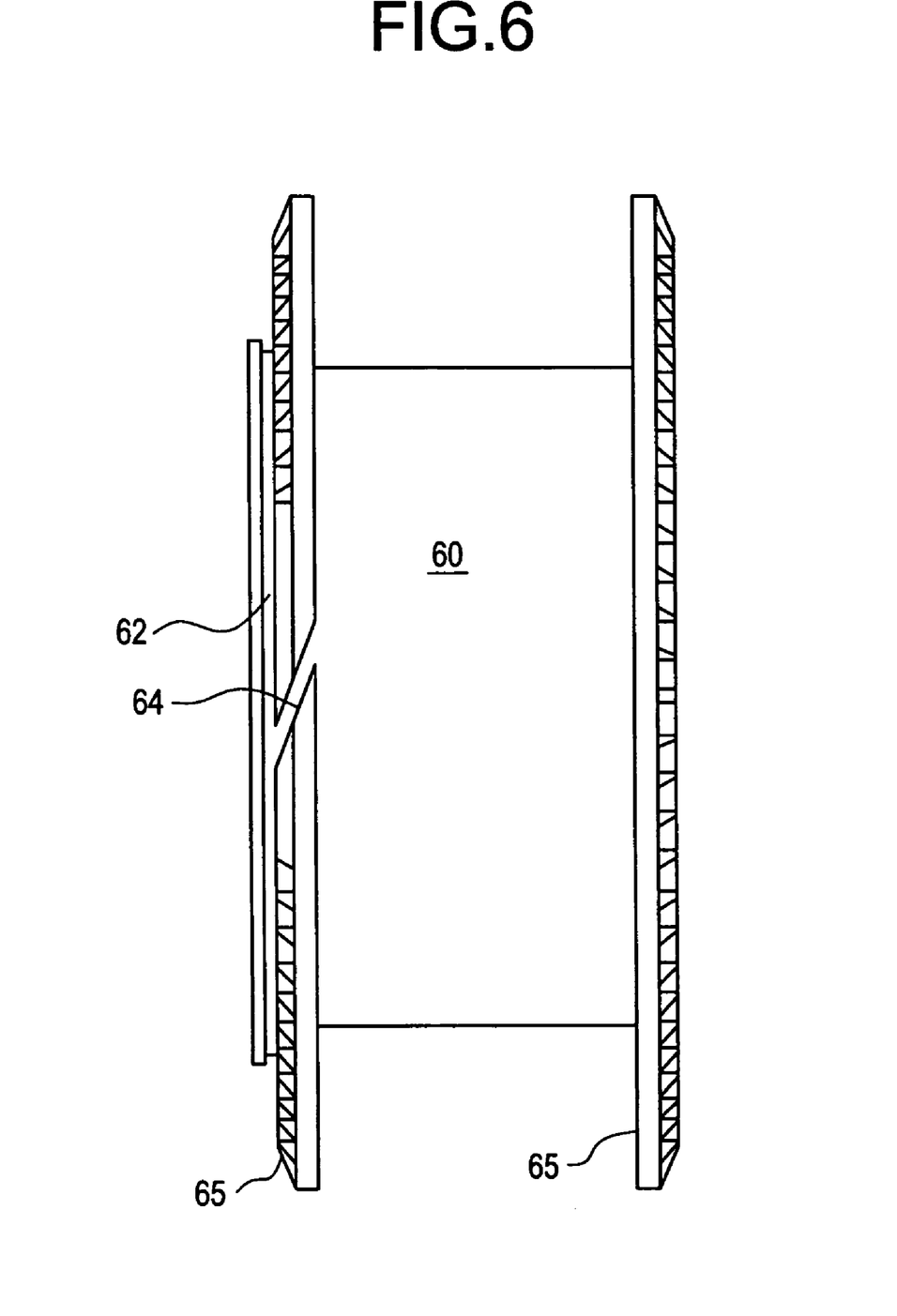
FIG. 6 illustrates a preferred fiber storage spool for use in accordance with the invention.

A preferred optical fiber storage spool which may be used in accordance with the invention is illustrated in FIG. 6, which shows side and bottom views of preferred shipping spool 15. As shown in FIG. 6, the spool 15 includes a primary barrel portion 60, and lead meter barrel portion 62, and an angled slot 64 through which fiber can be fed during the winding process from the lead meter portion 64 to the primary barrel portion 62, or vice versa depending on desired winding techniques. Such spools are described further, for example, in U.S. patent Ser. No. 09/438,112, filed Nov. 10, 1999, titled System and Method for Providing Under-Wrap Access to Optical Fiber Wound Onto Spools, which claims the benefit of U.S. Provisional Application Nos. 60/114,516, filed Dec. 30, 1998, and 60/115,540, filed Jan. 12, 1999, the specification of which is hereby incorporated by reference. In a preferred embodiment of the invention, the fiber is fed onto spool 15 beginning at lead meter barrel portion 62. When a desired amount of fiber has been stored on the lead meter portion 62, the fiber is then fed through the slot and onto primary barrel portion 60, and a desired amount of fiber is then wound onto primary barrel portion 60. Once the spool is full and/or a desired amount of fiber is contained within the primary barrel portion 60, the fiber is cut, e.g. between the fiber winding system and the fiber screening system and rotating turret 40 indexes 180 degrees to provide another empty storage spool 15 onto which fiber can again be wound. The previously filled spool is then removed, and an empty spool loaded in its place, and so forth, so that when the newly provided empty spool is filled, the next spool will ready, and so forth. One reason shipping spool 15 is preferred is that fiber may be stored on spool 15 in a manner which enables access to both ends of the fiber. Because the spool enables access to both ends of the fiber, optical and other testing can be conducted on the fiber which is stored on spool 15 after the fiber draw and winding process, without having to remove the entire length of fiber from the spool or rethread the fiber onto a different spool.

The system also includes aspirator 16, illustrated in FIGS. 1 and 2, which is used to remove scrap fiber from the process as well as to facilitate automated threading of the fiber onto the various components of the system at the beginning of the draw operation or after a fiber break, of after the fiber is intentionally cut, as will be further described below. As can be seen in FIGS. 1 and 2, aspirator 16 consists basically of a cylindrical tube such as a vacuum hose, and is movably attached to vertical support member 17 along which the aspirator can be moved in an upward or downward path. Such aspirators can, for example, use compressed air to provide the sucking force needed to suck fiber into aspirator 16. Preferably the compressed air has a velocity which is high enough to provide sufficient tension to capture and control movement of the fiber throughout the winding system as it is being rethreaded, as well as to convey away any scrap fiber. Vertical support member 17 is in turn movably mounted on transverse support member 18, which in turn is movably mounted on main aspirator support frame 19. In this way the aspirator can be moved in 3 dimensions, e.g., the aspirator can be moved closer to or further away from screener section 12 by the sliding of transverse support member 18 along the main support frame 19. The aspirator 16 can also be moved transverse to the main support frame (toward or away from the back of the machine system, i.e., parallel to the axis of the indexing spool winding 40) by sliding of the vertical suport member 17 along transverse support member 18.

Operation of the fiber winding system in accordance with the present invention is preferably controlled via a computer control system, which may be programmed to respond to various inputs, which may be either automatically sent from the winding system or manually inputted by a machine operator.

During the fiber draw operation, an optical fiber draw blank (also known as an optical fiber preform) is mounted in a draw furnace (not shown), and the temperature in the furnace is raised to a temperature suitable for drawing optical fiber from the preform. As can be seen in FIG. 2, screener section 12 includes a pair of capstan assemblies 20 and 24, each of which consist of a large capstan wheel and a belt which is in engagement with a portion of the circumference of the large capstan wheel. The belt is also supported by three smaller wheels, which are positioned so that the belt is held firmly against the larger capstan wheels. As used generally herein, capstan refers to such capstan assemblies as are illustrated in FIG. 2, although alternative capstan assemblies could also be employed without detracting from the spirit of the invention. Optical fiber 8 is pulled from the drawblank during the fiber draw operation by belted capstan 20, also known as and referred to herein as the tractor capstan, illustrated in FIG. 2. The speed of belted capstan 20 can be controlled by suitable control means to achieve a desired speed for drawing the fiber.

As shown in FIG. 2, in the embodiment illustrated, the fiber exits tractor capstan 20 and wraps 180 degrees around turn-around pulley 22. Turnaround pulley 22 has a recessed groove around its periphery within which the fiber 8 is retained. Turnaround pulley 22 is connected to a load cell which monitors the amount of tension applied onto the turnaround pulley by the passing fiber, and thus monitors the amount of tension being imparted to the fiber. From turnaround pulley 22, the fiber enters belted screener capstan 24. In the embodiment illustrated the screener capstan 24 is electronically "slaved" to tractor capstan 20 so that at all times it rotates slightly faster than tractor capstan 20. The speed differential between screener capstan 24 and tractor capstan 20 is maintained at a magnitude, which causes a desired amount of strain within the fiber. The strain imparted to the fiber is directly proportional to the tensile stress in the fiber. Any tension present in the fiber prior to entering the tractor capstan 20 is added to the tension caused by the differential speed of the two capstans 20 and 24. Depending on the speed at which the fiber is being drawn, the incoming tension during a normal blank run can vary by as much as 30 kpsi. Consequently, in a preferred embodiment, feedback from the load cell of the turnaround pulley 22 is used to adjust the differential speed of the screening capstan 24 so that a sufficient screening tension is maintained consistently throughout drawing of the entire optical fiber blank into optical fiber.

During the fiber draw process, fiber exits screener capstan 24 in screening section 12 and proceeds to winding section 14, which is illustrated in FIG. 3. In the embodiment illustrated, the fiber leaves screening capstan 24 in FIG. 2 at an angle which is approximately 30 degrees to the manufacturing plant floor, and proceeds to the winding section 14 illustrated in FIG. 3. At winding section 14, the fiber 8 is wound through four process pulleys 30a-30d before being wound onto fiber storage spool 15. In the embodiment illustrated, the first three process pulleys 30a-30c are disposed substantially within the same plane as the incoming fiber, in this case 30 degrees relative to the plant floor. The fiber wraps 90 degrees around the first pulley 30a and then 180 degrees around second pulley 30b, which is a dancer pulley. Dancer pulley 30b is attached to a pivot arm 32. Such dancer pulley mechanisms are described further, for example, in U.S. patent application Ser. No. 09/390,866, filed September 7, titled Passive Tension Regulator, the specification of which is hereby incorporated by reference.

From dancer pulley 30b, the fiber wraps 90 degrees around third pulley 30c and then around fourth pulley 30d, whose axis of rotation is perpendicular to that of the first three pulleys 30a-30c. The fiber wraps approximately 45 degrees around the fourth pulley 30d and then continues to the take up spool 15. Pulley 30d is oriented to redirect and guide fiber 8 onto take up spool 15. The third and fourth pulleys 30c and 30d are both mounted on traversing carriage 34 which traverses back and forth parallel to the axis of the take up spool 15 during the fiber winding operation to result in uniform winding of the fiber onto spool 15. Carriage 34 moves back and forth along a support bar (not shown), reciprocating parallel to the axis of spool 15. The movement of carriage 34 is preferably controlled via computer.

During the winding of the fiber onto spool 15, a constant torque is applied to the dancer pivot arm 32 in a direction which is opposite, or away from, first pulley 30a. Such a torque may be provide, for example, via a hydraulic air cylinder attached to dancer pivot arm 32. The torque applied to dancer pivot arm 32 and the speed with which the spool is rotated are controlled so as to wind the fiber onto the spool with a uniform winding tension applied to the fiber.

The angular position of dancer arm 32 is monitored and employed in conjunction with a control computer to control the rotating take up speed of the spool 15. A sensor senses the angular position of the second pulley 30b. In a preferred embodiment, the sensor is an RVDT. The position of the second or dancer pulley 30b is used to determine the difference between the speed at which the optical fiber is being supplied from screener section 12 and the speed at which the optical fiber is being wound on a spool. The speed at which the spool 15 is rotating can then be adjusted according to the speed of the optical fiber being supplied from screener section 12, so that the fiber is wound under the spool 15 with a uniform amount of tension. The vertical position of the second pulley 30b is also used to detect a break in the optical fiber, as the load cell attached to the second pulley 30b will register zero load when the optical fiber breaks.

As illustrated in FIG. 1, winder section 14 includes two independent spindles which each retain a take up spool 15. The spindles are mounted 180 degrees apart on an indexing turret 40. Winding of fiber only occurs to the spindle that is in the upper position. The lower position is used to hold an empty spool that is ready in the event of a fiber break.

The breaks that occur during a fiber draw operation can be broken down into two basic categories, pre-screener breaks, which are breaks that occur in the fiber before the fiber has reached the screener capstan 24, and post-screener breaks, which are breaks that occur in the fiber after the fiber has passed the screener capstan 24. By monitoring the load cells attached to turnaround pulley 22 and the position of dancer arm 32, the control computer can control operation of the winding system and react to breaks which occur at various points in the winding operation. For example, when a pre-screener break occurs, the load cell on turnaround pulley 22 will almost immediately register zero load. Consequently, when the computer senses that the load at turnaround pulley is zero, the computer initiates a control sequence for rethreading of the fiber through the screener capstan as well as the remainder of the winding system.

In a preferred embodiment of the invention, several simultaneous fiber threading actions occur at the screening section and at the winding section of the machine when a pre-screener break is detected. The actions at the screener section will be described first, followed by the winder section description.

Threading of the Screener Section

Figure 4A:
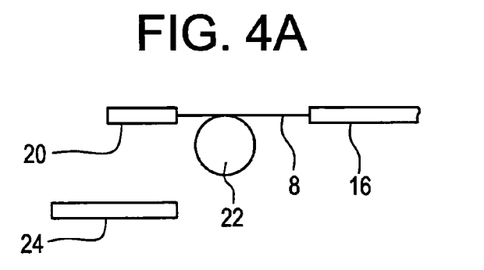
FIGS. 4A-4E are top plan views of the winding apparatus of FIG. 1, illustrating the optical fiber being threaded onto the screener capstan.

In normal operational mode, while fiber is being drawn and wound onto spool 15, the nozzle of aspirator 16 is positioned adjacent the fiber path as it exits tractor capstan 20 traveling toward winder section 14. When a fiber break occurs between the tractor and screener capstan, the fiber down stream of the break is pulled through the four remaining process pulleys downstream and onto the take up spool. The computer immediately detects the fiber break via the turnaround pulley load cell, registering zero load. With nothing to guide it, fiber exiting the tractor capstan is pushed out from the capstan in a straight line. Aspirator 16 may be positioned such that the fiber streaming from the tractor capstan will be sucked into the nozzle of the aspirator 16, as illustrated in FIG. 4A. Alternatively, aspirator 16 can be positioned at a location which is remote from the path of the fiber, and after a fiber break occurs, the aspirator can be moved into a position in which it collects the fiber.

High pressure air is supplied to the aspirator 16 from an electronically controlled proportional air valve, and the pressure to aspirator 16 creates a vacuum at the aspirator nozzle, and the vacuum pulls the fiber into the aspirator 16. The fiber exits the aspirator into a fiber collection can. The amount of time between a prescreener break and acquisition of the fiber by the aspirator is only a fraction of a second due to the fact that the aspirator is positioned nearly in line with the path of the fiber during normal winding operation. Of course, the aspirator could be positioned further away from the path of the incoming fiber and the aspirator vacuum increased until such time as the fiber is captured by the aspirator.

Consequently, almost immediately after a prescreener break occurs, the fiber is being sucked into aspirator 16. The aspirator is then moved in accordance with the invention to facilitate rethreading of the fiber through the screener capstan. As illustrated in FIG. 1, the aspirator is movable along three motorized linear axes 17, 18 and 19 (and thereby is movable in three dimensions) to facilitate threading of the entire machine.

Figure 4B:
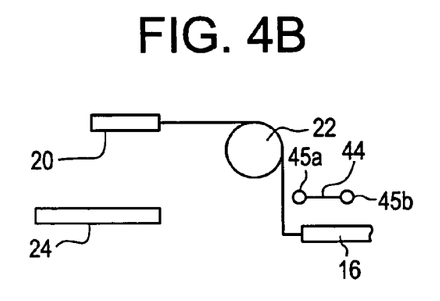

The screener capstan rethreading sequence is illustrated with reference to FIGS. 1 and 4A-4E. It should be noted that FIGS. 4A-4E are only schematic, and actual relative dimensions have been altered to facilitate illustrations of the invention. Once fiber 8 is acquired by aspirator 16, a rethreading sequence is initiated to rethread the turnaround pulley 22 and the screener capstan 24. To accomplish this, the aspirator may be positioned or moved to be positioned essentially in line with fiber exiting the tractor capstan, as illustrated in FIG. 4A, so that the aspirator begins to collect the fiber exiting the capstan 24. The aspirator is then moved along transverse support member 18 to guide the fiber onto the groove of turnaround pulley 22 and wrap the fiber around 90 degrees of turnaround pulley 22, as illustrated in FIG. 4B. Threading of the final 90 degrees of turnaround pulley 22 and the screener capstan is preferably done using a guide finger system 44, as shown in FIG. 2. Guide finger system 44 consists of at least one, and preferably a pair of guide fingers 45a and 45b. These finger-like guide fingers do not grasp the fiber, but rather enable the fiber to slide around their outer periphery and into the aspirator, where it is continuously discarded. This process facilitates rethreading of the fiber while the fiber continues to be drawn during the fiber draw operation. The guide fingers may be for example, a pair of cylindrical metal tubes which may or may not be rotatable around their axis to facility transport of the fiber over the surface of the guide fingers. The guide fingers are moved up and down via Z-axis support bars 46 and back and forward (left and right) along X-axis support member 47, by pneumatic slides. The second guide finger 45b also has a pneumatic slide 48 that allows motion in and out (Y axis). The guide fingers 45a and 45b are in the Z-up, X-forward (toward the winder section), and Y-in position, as illustrated in FIG. 2, prior to the initiation of the rethreading sequence. Once the aspirator has threaded 90 degrees of turnaround pulley 22, the guide fingers are moved to the Z down position so that both guide fingers are behind the line of fiber going into the aspirator from the turnaround pulley, as illustrated in FIG. 4B.

Figure 4C:
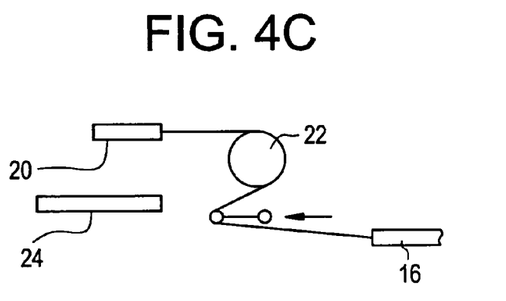
Figure 4D:
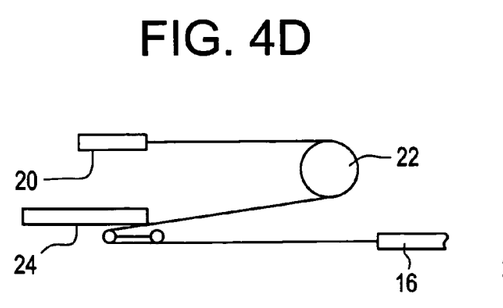
Figure 4E:
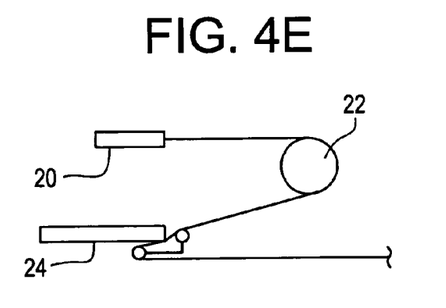

The guide fingers 45a and 45b are then moved toward the X-back (away from the winder section) position so that threading of the screener capstan can take place. As the guide fingers 45a and 45b are moved in this manner, guide finger 45a engages fiber 8 and moves it toward screener capstan 24. At the same time, guide fingers 45a and 45b are moving to rethread the screener capstan 24, aspirator 16 begins moving toward the winder section 14 to begin rethreading of winder section 14, as illustrated in FIG. 4C. This action allows for faster rethreading of the entire system as two portions of the machine, the screener section 12 and the winder section 14, are being threaded simultaneously. Guide fingers 45a and 45b continue until first guide finger 45a is adjacent screener capstan 24, at which point the fiber path is almost 180 degrees around turnaround pulley 22, 180 degrees around first guide finger 45a, and into the aspirator which is still moving to a position behind the fiber take up spool 15 as illustrated in FIG. 4D. At this point, the second guide finger 45b moves to the Y-out position i.e., toward screener capstan 24, as illustrated in FIG. 4E. Guide finger 45b urges the fiber into the area of the screener capstan where the belt and the capstan meet. The screener capstan may also be provided with one or more nubs or snagger hooks that are positioned on the outer diameter of the capstan. As the capstan rotates, the nubs can help urge the fiber into the area where the belt and capstan meet. Once the fiber is captured between the belt and capstan, the fiber is carried around the capstan, below and out of engagement with the first guide finger 45a as it is carried around the screener capstan. At this point guide finger 45b retracts, and the threading of screener section 12 is complete, with the fiber traveling around turnaround pulley 22 and screener capstan 24. The result is that the turnaround pulley 22 and screener capstan 24 are threaded without breaking the line of fiber, which is traveling into the aspirator. Guide fingers 45a and 45b are then returned to the Y-in, Z-up, and X-forward positions.

Threading of the Winder Section

Figure 5A:
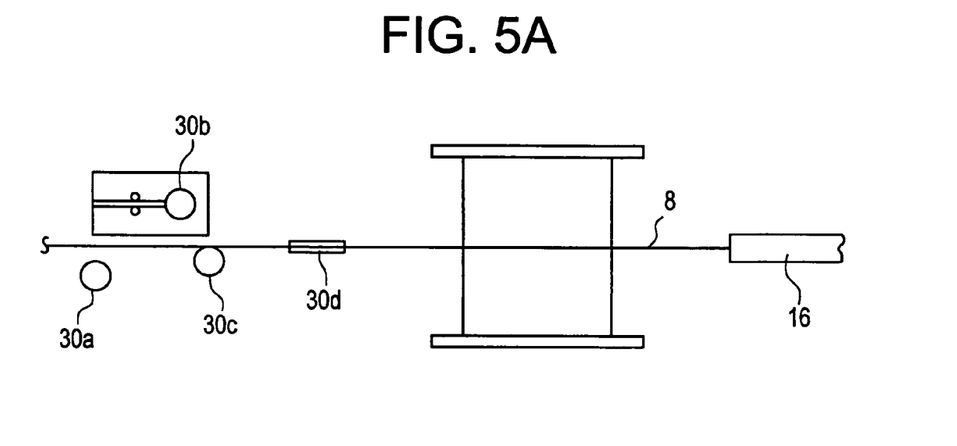
FIGS. 5A-5C are top plan views of the winding apparatus of FIG. 1, illustrating threading of the optical fiber through the winder section.

Threading of the winder section 14 preferably takes place simultaneous with the threading of the screener section 12. Thus, referring to FIG. 3, when a pre-screener break is detected by the turnaround pulley 22 load cell, the first actions of winder section 14 occur simultaneously to facilitate threading of the winding section by the aspirator. In FIG. 3, a pair of rotatable fiber storage spools 15 are mounted 180 degrees apart on turret 40. In the embodiment illustrated, only one of the spools 15 is visible, and is collecting fiber being supplied via the fiber draw process. The other fiber storage spool 15 is positioned 180 degrees, or directly underneath the spool 15 which is visible. The other spool 15 is empty and ready to be moved into position to receive fiber from the fiber draw process. Also visible in FIG. 3 is dancer platform 34, upon which dancer pulley 30b is mounted via armature 32. Dancer platform 34 is movable along a transverse slide (not shown), from the closed position illustrated, in which dancer pulley 30b is engaging fiber 8 and forcing fiber 8 to take a serpentine path, to an open position, in which dancer pulley 30b is moved and positioned on the other side of the path of fiber 8. In FIG. 3, dancer pulley 30b is shown in the closed position. Likewise, pulley 30c is mounted on a traverse (not shown), which is capable of moving pulley 30c into and out of engaging position with the path of fiber 8. As mentioned above, while the guide fingers 45a and 45b are moving the fiber 8 toward screener capstan 24 to thread the screener 24, aspirator 16 and thus fiber 8 are simultaneously moved toward the winding section 14. At the same time, three things preferably occur simultaneously:

(1) the winder turret 40 indexes 180 degrees so that a new empty fiber storage spool 15 is in place for winding;
(2) the new spool 15 begins rotating slightly faster than the linear speed of the incoming fiber; and (3) the pulley 30*a*, dancer pulley 30*b* and pulley 30*c* are moved on their respective traverse slides into an open position (as shown in FIG. 5*a*) to enable threading of the fiber 8 through winder section 14. For this to occur pulley 30*c* is moved along its own pneumatic slide toward a position outboard of the fiber path.

The dancer stops 33 come together to hold the dancer arm 32 in a fixed position, and the dancer slide (not shown) moves the dancer platform 34 toward the inboard position of the path to be taken by the fiber. Pulley 30*a* is moved along pneumatic slide 57 to a position outboard of the path to be taken by the fiber.

As can be seen in FIG. 3, the winder section was designed so that the aspirator 16 can pass freely above all of the winder components while fiber is being pulled into the aspirator nozzle. The aspirator 16 moves to a position that is above and behind the take up spool 15. Aspirator 15 then moves downward, guiding the fiber 8 onto the fourth process pulley 30*d*. The aspirator continues moving down until the line of fiber coming from pulley #4 is tangent to the barrel of the take up spool. At this point the winding section is as illustrated in FIG. 5*a*.

Figure 5B:
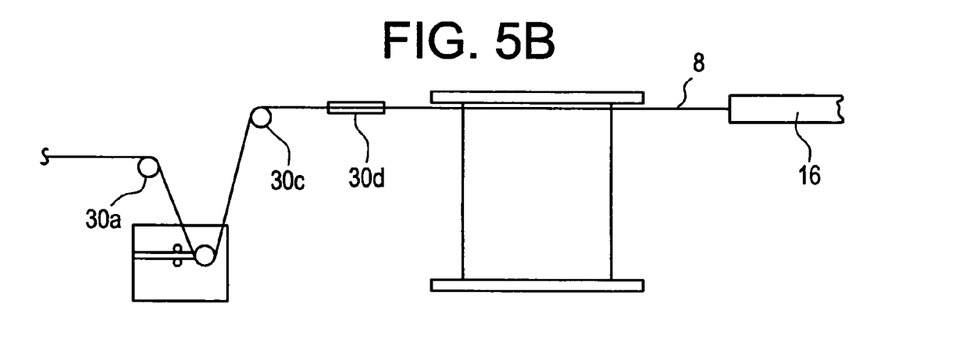
Figure 5C:
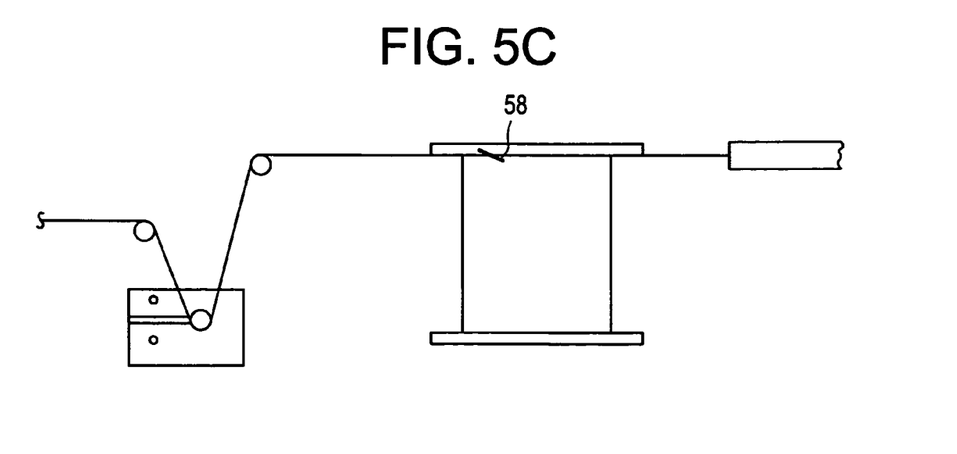

When the aspirator has threaded fiber 8 onto the pulley 30*d* and the fiber is tangent to the barrel of the spool 15, pulleys 30*a*, 30*b*, and 30*c* are moved to their normal run position. Thus, as illustrated in FIG. 5*b*, pulleys 30*a* and 30*b* move into contact with the fiber. The dancer slide then moves the dancer pulley 30*b* toward a position which is outboard of the path of the fiber. This action brings the fiber path to its normal running position illustrated in FIG. 5*b*, namely, approximately 90 degrees around pulley 30*a*, 180 degrees around pulley 30*b*, 90 degrees around pulley 30*c* and approximately 15 degrees around pulley 30*d*. The dancer stops are moved to their run position and the dancer is forced to the outboard stop.

Spool 15 is then traversed to bring the fiber into contact with a snagger tooth 58, which is present on the flange of spool 15. The fiber is wedged into the snagger and cut, separating the fiber from the aspirator and beginning the winding of the fiber onto spool 15. The dancer is initially pulled toward the inboard position of the winder due to the over spinning of the take up spool. The speed of the rotation of the take up spool 15 may be controlled by the dancer position and the speed adjusted so that the dancer arm is pulled to a nominal running position. The aspirator then moves back to the staged position, which is proximate to in line with the fiber exiting the tractor capstan.

The spool that was taking up fiber before the break is automatically unloaded from the bottom of the winder turret 40, and a new empty spool is loaded into the spindle. The machine is then ready for the next fiber break event.

Cases also exist where the fiber is broken somewhere between the screener capstan and the take up spool. The first case may be when the take up spool is full. A second case occurs when the fiber is detected that is out of specification (e.g. the diameter is too large or too small). In either of these two cases, an automatic fiber cutter intentionally cuts the fiber. Such a mechanical cutting device may be positioned, for example, just before the fiber enters the first process pulley 30*a*. A third case of a post screener break occur when something unexpected causes the fiber to break (stray fiber, nicked process pulley, etc. . . ) after the screener capstan 24.

The only difference in the threading sequence between a post screener break and a pre-screener break is that the screener section does not need to be rethreaded. In the case of a post screener break, the fiber is carried out of the screener capstan in a straight line. The aspirator is moved to a position adjacent the screener capstan so that the fiber can be captured by its vacuum. Once captured, the machine goes through the winder section threading sequences described above, as if it were a screener break, except that no actions need be performed to thread the screener capstan since it is still threaded.

A control system for controlling the winding apparatus 10 to perform the above-mentioned threading and winding operations is preferably also provided. The control system preferably includes a programmable logic controller to control the operation of the various sequence of events, monitor all of the sensors (e.g., the load cell on turnaround pulley 20 and the load applied by the fiber to dancer 34). The logic controller may also be used to control air cylinders which are used to move various components (e.g. pulleys 30*a*-30*c*) into position, as well as to communicate with a motion control computer. The motion control computer preferably controls and monitors the moving mechanisms such as aspirator 16, guide fingers 45A and 45*b*.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A method of threading a moving length of optical fiber through a component in an optical fiber draw, optical fiber winding or optical fiber testing process, comprising:

activating an aspirator to obtain said optical fiber at a first location and moving said aspirator in at least two dimensions to move said optical fiber to a second location to thread said optical fiber through a component in said optical fiber draw process.

2. The method of claim 1, wherein said moving length of optical fiber is a moving length of optical fiber in an optical fiber draw process, and said method further comprises orienting at least a first, second, and third pulley so that, when said aspirator moves said optical fiber to said second location, said pulleys are disposed along the length of said optical fiber and on alternating sides of said optical fiber, and said method further comprises moving said second pulley across the path of said optical fiber to retain said optical fiber in contact with said first, second, and third pulleys, thereby causing said optical fiber to move in a serpentine path.

3. The method of claim 1, wherein said aspirator is moved to guide said optical fiber onto at least one guide pulley by said aspirator guiding said optical fiber between or against a pair of surfaces which are disposed on each side of said guide pulley, said surfaces sloping toward said guide pulley to thereby guide said optical fiber onto said guide pulley.

4. The method of claim 2, wherein said aspirator is moved to guide said optical fiber onto at least one guide pulley by said aspirator guiding said optical fiber between or against a pair of surfaces which are disposed on each side of said guide pulley, said surfaces sloping toward said guide pulley to thereby guide said optical fiber onto said guide pulley.

5. The method of claim 1, wherein said second location is proximate to a optical fiber winding spool.

6. The method of claim 5, further comprising engaging said optical fiber at a point along said optical fiber which is between the aspirator and the source of optical fiber, and winding said engaged optical fiber onto said spool.

7. The method of claim 6, wherein said engaging said optical fiber comprises engaging said optical fiber by a snagger tooth which is located on said spool.

8. The method of claim 1, further comprising engaging said optical fiber at a point along the length of said optical fiber which is between the source of said optical fiber and said aspirator, and moving said engaged optical fiber to facilitate threading of said optical fiber through said at least one component of said optical fiber draw process.

9. The method of claim 8, wherein said engaging an optical fiber step comprises engaging a moving length of optical fiber, moving said engaged length of moving optical fiber into contact with a capstan to thereby thread said optical fiber around said capstan.

10. The method of claim 9, wherein simultaneous with said threading of said capstan, said aspirator is moving to said second location, and said second location is proximate to a winding spool.

11. The method of claim 10, wherein said moving length of optical fiber is a moving length of optical fiber in an optical fiber draw process, and said method further comprises orienting at least a first, second, and third pulley so that, when said aspirator moves said optical fiber to said second location, said pulleys are disposed along the length of said optical fiber and on alternating sides of said desired optical fiber, and said method further comprises moving said second pulley across the path of said optical fiber to retain said optical fiber in contact with said first, second, and third pulleys, thereby causing said optical fiber to move in a serpentine path.

12. The method of claim 11, further comprising moving said aspirator to guide said optical fiber onto at least one guide pulley by said aspirator guiding said optical fiber between or against a pair of surfaces which are disposed on each side of said guide pulley, said surfaces sloping toward said guide pulley to thereby guide said optical fiber onto said guide pulley.

* * * * *